United States Patent [19]
Bridges et al.

[11] Patent Number: 6,133,742
[45] Date of Patent: Oct. 17, 2000

[54] MULTI-PULSE SAMPLING OF SIGNALS USING ELECTROSTATIC FORCE SAMPLING

[75] Inventors: Greg E. Bridges; Doulgas J. Thomson, both of Winnipeg, Canada

[73] Assignee: Micron Force Instruments, Inc., San Jose, Calif.

[21] Appl. No.: 09/159,398

[22] Filed: Sep. 23, 1998

Related U.S. Application Data

[60] Provisional application No. 60/063,171, Oct. 24, 1997.
[51] Int. Cl.⁷ .................................................. G01R 31/00
[52] U.S. Cl. .......................... 324/676; 324/762; 324/72; 324/458
[58] Field of Search .............................. 324/676, 72, 456, 324/458, 537, 73.1; 73/105

[56] References Cited

U.S. PATENT DOCUMENTS

| | | | |
|---|---|---|---|
| 4,992,728 | 2/1991 | McCord et al. | 324/158 |
| 5,381,101 | 1/1995 | Bloom et al. | 324/676 |
| 5,481,908 | 1/1996 | Gamble | 73/105 |
| 5,488,305 | 1/1996 | Bloom et al. | 324/537 |
| 5,959,447 | 10/1999 | Bridges et al. | 324/762 |

OTHER PUBLICATIONS

E.W. Strid and T. Burchman, "Wideband Probing Techniques for Planar Devices," Solid State Tech., Aug. 1989.

J. Kim, et al., Photoconductive Sampling Probe with 2–3 ps Temporal Resolution and 4–\mu V Sensitivity, Appl. Phys. Lett., vol. 62, May 1993.

P. G. May, et al., "Noncontact High–Speed Waveform Measurements with the Picosecond Photoelectron Scanning Electron Microscope," IEEE J. Quantum Electron., vol. 24, Feb. 1988.

H.K. Wickramasinghe, "Scanned–Probe Microscopes," Sci. Am., pp. 98–105, Oct. 1989.

Y.A. Martin, et al., "High–Resolution Capacitance Measurement and Potentiometry by Force Microscopy," Appl. Phys. Lett., vol. 52, Mar. 1988.

J.M.R. Weaver, and David W. Abraham, "High Resolution Atomic Force Microscopy Potentiometry," J. Vac. Sci. Techol. B., vol. 9, May/Jun. 1991.

R.A. Said, et al., "Noninvasive Scanned Probe Potentiometry for Integrated Circuit Diagostics," IEEE Trans. Instrum. Measure, vol. 43, Jun. 1994.

A.S. Hou, et al., "Picosecond Electrical Sampling Using a Scanning Force Microscopy," Electron. Lett., vol. 28, Dec. 1992.

(List continued on next page.)

*Primary Examiner*—Safet Metjahic
*Assistant Examiner*—T. R. Sundaram
*Attorney, Agent, or Firm*—Blakely Sokoloff Taylor & Zafman, LLP

[57] ABSTRACT

A method and an apparatus for providing non-contact measurement of waveforms proximate to a surface of a sample. In one embodiment, the described apparatus includes a composite probe waveform generator configured to provide a composite probe waveform having a plurality of overlapping component probe waveforms. Each of the overlapping component probe waveforms have a repetition rate substantially equal to the repetition rate of the sample waveform to be measured from the sample. The apparatus includes a cantilever with a signal path to carry the composite probe waveform to a position above the sample surface where the sample waveform is to be measured. In one embodiment, each of the component probe waveforms of the composite probe waveform is modulated at a frequency near a mechanical resonance frequency of the cantilever. Capacitive coupling between the cantilever and the signal line of the sample results in a periodic motion of the cantilever at a rate determined by the modulation frequencies of the component probe waveforms. By detecting the motion of the cantilever, and sorting out the excitation from the different overlapping component probe waveforms, the sample waveform can be determined.

24 Claims, 8 Drawing Sheets

OTHER PUBLICATIONS

G.E. Bridges, et al., "Heterodyne Electrostatic Force Microscopy for Non–contact High Frequency Integrated Circuit Measurement," Electron Lett, vol. 29, Aug. 1993.

R.A. Said, et al., "Scanned Electrostatic Force Microscope for Noninvasive High Frequency Potential Measurement," Appl. Phys. Lett., vol. 64, Mar. 1994.

C. Bohm, et al., "Voltage Contrast in Integrated Circuits with 100nm Spatial Resolution by Scanning Force Microscopy," J. Phys. D.: Appl. Phys. vol. 25, 1993.

D.M. Bloom, "Voltage–Contrast Scanning Probe Microscopy," Microelectronic Engineering, vol. 24, 1994.

G.E. Bridges, et al., "Sampled Waveform Measurement in Integrated Circuits Using Heterodyne Electrostatic Force Microscopy," Rev. Sci Instrum., vol. 65, Nov. 1994.

G.E. Bridges, & D.J. Bridges, et al., "High–Frequency Circuit Characterization using the AFM as a Reactive Near–Field Probe," J. Ultramicroscopy, vol. 42, 1992.

K. Domaniski, et al., "Mapping of Mobile Charges on Insulator Surfaces with the Electrostatic Force Microscope," Appl. Phys. Lett., vol. 63, Sep. 1993.

R.A. Said, Scanning Force Potentiometry Techiques for Semiconductor Circuit Characterization, Thesis, Dept. of Elect. & Comp. Eng., Univ. of Manitoba, Canada, 1995.

D. Noruttun, Non–contact Internal Probing of High Speed Microelectronic Circuits Using Electrostatic Force Microscopy, Thesis, Dept. of Elect. & Comp. Eng., Univ. of Manitoba, Canada, 1997.

"Advanced Electro–optic Sampling Permits Non–invasive Testing of IC Performance," Electronic Engineering, Feb. 1989.

S.S. Osofsky, "Design and Performance of a Non–Contacting Probe for Measurements on High–Frequency Planar Circuits," IEEE Trans on Microwave Theory and Tech., vol. 40, Aug. 1992.

M. Nonnenmacher, et al., "Kelvin Probe Force Microscopy," Appl. Phys. Lett., vol. 58, Jun. 1991.

F. Ho, et al., "High–Speed Integrated Circuit Probing Using a Scanning Force Microscope Sampler," Electronics Letters, vol. 30(7), Mar. 1994.

G.E. Bridges, et al., "Novel Near–Field Probe for On–Wafer Integrated Circuit Measurements," Microelectronics J, vol. 23(5), 1992.

G.E. Bridges, et al., "High–Frequency Pattern Extraction in Digital Integrated Circuits Using Scanning Electrostatic Force Microscopy," J. Vac. Sci. Techol. B, vol. 13(3), May/Jun, 1995.

A. Leyk, et al., "104GHz Signals Measured by High Frequency Scanning Force Microscope Test System," Electroics Letters, Apr. 1995.

R. Said, "Non–Contact Probing of High Speed Microelectronics," Dept. of Electrical and Computer Engineering, U. of Manitoba, Canada.

R. Said and G. Bridges, "Heterodyne Electrostatic Force Microscopy Used as a New Non–Contact Test Techique for Integrated Circuits," Dept. of Electrical and Computer Engineering, U. of Manitoba, Canada, 1995.

R. Said, et al., High Frequency Potential Probe Using Electrostatic Force Microscopy, J. Vac. Sci. Techol. A vol. 12(4), Jul./Aug., 1994.

C. Bohm, et al., "Contactless Electrical Characterization of MMICs by Device Internal Electrical Sampling Scanning––Force–Microscopy," IEEE MTT–S Digest, 1994.

C. Bohm, et al., "Scanning–Force–Micrscope Test System for Device Internal Test with High Spatial and Temporal Resolution," Microelectron. Eng., vol. 24, 1994.

A.S. Hou, et al., "Scanning Probe Microscopy for Testing Ultrafast Electronic Devices," Optical and Quantum Electronics, vol. 28, 1996.

B.A. Nechay, et al., "Applications of an Atomic Force Microscope Voltage Probe with Ultrafast Time Resolution," J. Vac. Sci. Techol. B, vol. 13(3), May/Jun. 1995.

MULTI-PULSE SAMPLING OF SIGNALS USING ELECTROSTATIC FORCE SAMPLING

RELATED APPLICATIONS

This application claims priority to U.S. provisional application Ser. No. 60/063,171, filed Oct. 24, 1997, entitled "Non Contact Measurement Of Electrical Waveforms On The Surface Of A Sample Using Time Domain Gating," and assigned to the assignee of the present invention.

This application also claims priority to U.S. application Ser. No. 09/020,173, filed Feb. 6, 1998, now U.S. Pat. No. 5,959,447, issued Sep. 28, 1999, entitled "Non Contact Measurement Of Electrical Waveforms On The Surface Of A Sample Using Time Domain Gating," and assigned to the assignee of the present invention.

BACKGROUND OF THE INVENTION

Field of the Invention

The present invention relates generally to waveform measurements and, more specifically, the present invention relates to the measurement of electrical waveforms proximate to the surface of a sample such as for example an integrated circuit.

Background Information

The microelectronics field is a multi-billion dollar industry that is driving rapid technological advances in the fabrication of dense high frequency integrated circuits. Within this industry there is a continuing effort to increase integrated circuit speed as well as device density. The continuing technological advances create major challenges for researchers in the test and measurement field. For instance, the ability to measure the internal signals of a circuit is often important in order to perform design test, diagnostics and failure analysis of advanced microelectronics. High spatial and temporal resolution, non-invasiveness, and accuracy are among the desirable characteristics of a suitable measurement instrument. As circuit operating frequencies continue to increase and as device dimensions continue to decrease, these desirable characteristics of measurement instruments become increasingly difficult to achieve.

Present day measurement and probing methods based on direct physical contact of internal signal lines of a chip are often not suitable for internal testing of many circuits due to probe contact area, spatial limitations and/or the parasitic loading caused by the probe. Other disadvantages associated with probing methods based on direct physical contact of internal signal lines of a chip include circumstances where test points are not readily accessible, the electrical contacts of the test points are unreliable, the direct contact probe tip sizes are excessive in size and the removal of passivation layers are necessary to expose the test points.

Several non-contact measurement techniques, however, have been developed as alternatives to direct contact probing. Among the non-contact measurement techniques are electro-optic probing, opto-electronic sampling, reactive near-field probing, high-speed photo-emission sampling, and electron-beam testing. Several of these methods are capable of providing very high spatial and/or temporal resolution. However, these methods rely on measuring a secondary effect of the local circuit potential, which require complex calibration procedures thereby making accurate voltage measurements difficult and in some cases impossible. Furthermore, many of the above-listed instruments also require very specialized operating environments. For example, electron-beam testing must be performed in a vacuum.

In the last decade, several new measurement techniques based on scanning force have been utilized for non-contact measurements. One of the instruments that use the new measurement techniques is the electrostatic force microscope (EFM), which is capable of measuring static or low frequency voltages on the integrated circuits with very high spatial resolution. An advantage of the EFM approach is that it is simple and can be performed in air over passivated circuits. Until very recently, however, the technique has been limited to measuring only signals at repetition rates at, near or below the mechanical response of the probe, which is typically less than 100 KHz. As can be appreciated, many microelectronic measurement applications require higher frequency measurement capabilities in order to be useful.

A number of new techniques have been proposed to overcome the frequency limitations of the EFM. These new techniques have been used with varying degrees of success in proposed non-contact probing instruments that are able to perform both high speed digital signal and high frequency vector analog signal measurements. However, a number of difficulties and disadvantages still remain with the proposed probing instruments. For instance, accurate voltage measurements require precise probe positioning and calibration at every measurement location. The proposed probing instruments are subject to non-repetitive direct current (DC) voltage offset effects. Long bit pattern measurements are subject to signal-to-noise reduction. The equivalent-time bandwidth is limited at high frequencies due to probe mechanical frequency response and is subject to noise at low frequencies. Furthermore, the proposed techniques require expensive equipment and/or electronic components to implement or are band limited due to the unavailability of wide band components. Moreover, the need for calibration makes it difficult to use some of the above-listed methods for passivated circuits.

Therefore, what is desired is a method and an apparatus for providing measurement of electrical waveforms from a sample such as for example an integrated circuit. Such a method and apparatus should measure the electric signals from the surface of the sample without coming in direct physical contact with the sample. In addition, such a method and apparatus should provide measurement of high frequency signals without the need for expensive equipment and/or electronic components to implement.

SUMMARY OF THE INVENTION

A method and an apparatus for measuring a sample waveform in a signal line proximate to a surface of a sample is disclosed. In one embodiment, the apparatus includes a cantilever having a tip disposed near and spaced apart from the surface of the sample such that the tip of the cantilever is capacitively coupled to the signal line. The apparatus also includes a composite probe waveform generator to generate a composite probe waveform coupled to the tip of the cantilever. The composite probe waveform includes first and second probe waveform components, which are to be modulated at first and second modulation frequencies, respectively. In one embodiment, the first and second probe waveform components have first and second probe repetition rates, which are substantially equal to a sample repetition rate of a sample waveform. In one embodiment, the first and second modulation frequencies are substantially less than the sample repetition rate. In one embodiment, the apparatus also includes a motion detector coupled to the cantilever to detect a motion of the cantilever. Additional features and benefits of the present invention will become apparent from the detailed description, figures and claims set forth below.

BRIEF DESCRIPTION OF THE DRAWINGS

The present invention is illustrated by way of example and not limitation in the accompanying figures.

DETAILED DESCRIPTION

Figure 1:
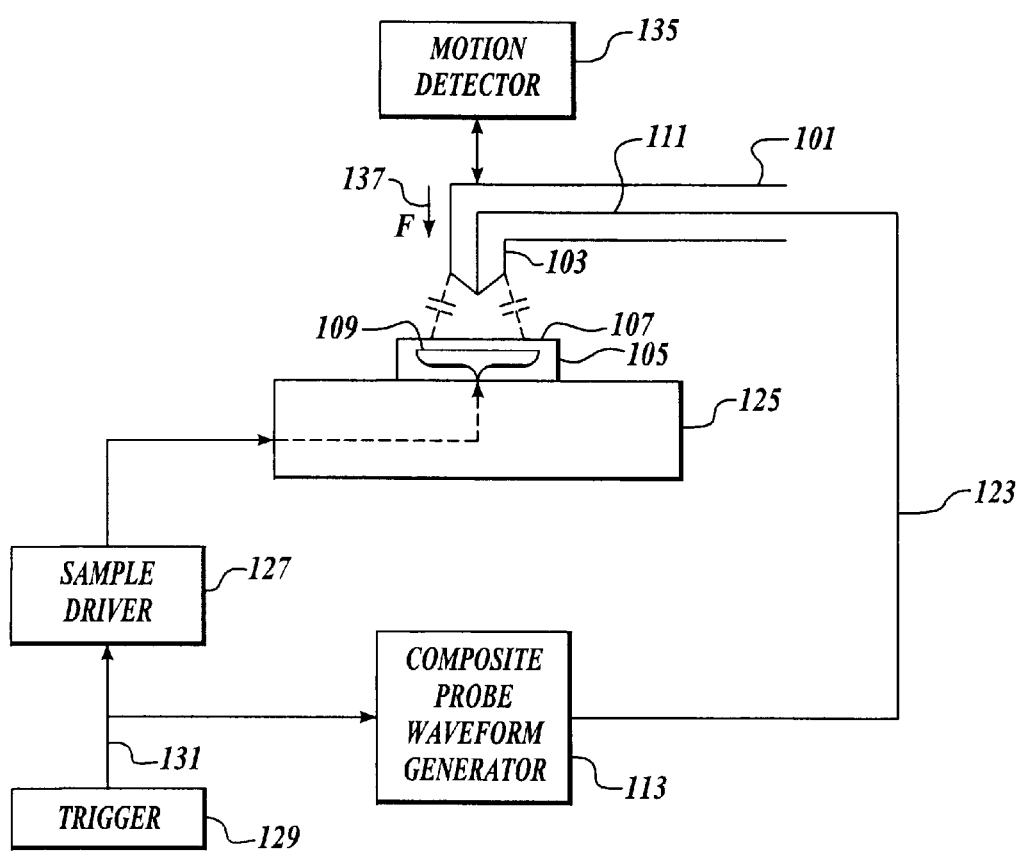
FIG. 1 is a block diagram of one embodiment of a non-contact waveform measurement apparatus in accordance with the teachings of the present invention.

A method and an apparatus for measuring a sample waveform in a signal line proximate to a surface of a sample is disclosed. In the following description, numerous specific details are set forth in order to provide a thorough understanding of the present invention. It will be apparent, however, to one having ordinary skill in the art that the specific detail need not be employed to practice the present invention. In other instances, well-known materials or methods have not been described in detail in order to avoid obscuring the present invention.

One embodiment of the present invention is an apparatus for measuring a periodic electrical signal waveform on or near the surface of a sample such as for example an integrated circuit. In one embodiment, the periodic electrical signal is sampled using several overlapping probe waveforms. The overlapping probe waveforms in one embodiment have substantially the same repetition rate or frequency as the sample electrical waveform to be measured from the sample. In one embodiment, the probe waveforms are electrical pulse trains. In other embodiments, it is appreciated that the probe waveforms may be other types of waveforms such as for example but not limited to sine waves, triangle waves, etc.

In one embodiment, the presently described apparatus also includes a cantilever that carries the overlapping probe waveforms to a tip of the cantilever, which is positioned above the sample surface where the sample signal to be measured is carried by the signal line. In one embodiment, the overlapping probe waveforms that are used to sample the signal from the sample are modulated at separate frequencies, which have periods much longer than the sample signal period. In one embodiment, the modulation frequencies are different from one another but are near a mechanical resonance frequency of the cantilever so as to provide an improved response.

In one embodiment, capacitive coupling between the cantilever and the signal line causes periodic mechanical motion in the cantilever at a number of repetition rates including DC, the modulation frequency repetition rate, and/or multiples thereof. In one embodiment, the periodic mechanical motion of the cantilever is measured at the various modulation frequency repetition rates and the electrical sample waveform carried by the signal line beneath the cantilever is measured accordingly. In another embodiment, the cantilever motion at the resonant frequency may be measured using known techniques to measure the sample waveform in accordance with the teachings of the present invention.

In another embodiment where the overlapping probe waveforms are electrical pulse trains, the mechanical motion of the cantilever will be approximately proportional to the magnitude of the electrical waveform carried in the signal line under the tip of the cantilever at the time when the pulses of the probe signals arrive at the tip of the cantilever. By varying the time at which the pulses of the probe signals arrive at the end of the cantilever by adjusting the time delay or phase of the probe waveforms, the amplitude of the electrical sample signal over the entire sample waveform period can be measured.

FIG. 1 is a block diagram of one embodiment of a non-contact waveform measurement apparatus in accordance with the teachings of the present invention. As illustrated in FIG. 1, a cantilever 101 having a tip 103 is disposed near and spaced apart from a surface 107 of a sample 105. It is appreciated that tip 103 may the end of the cantilever 101 or may simply be the portion of cantilever 101 that is near surface 107 of sample 105 in accordance with the teachings of the present invention. In one embodiment, cantilever 101 is free at the end of tip 103 and is fixed at the other end. In one embodiment, cantilever 101 may be constructed from a wire, a micro-machined beam, or the like.

In one embodiment, sample 105 is mounted on a stage 125. A sample driver 127 drives a periodic sample waveform through a signal line 109, which in one embodiment is proximate to surface 107 of sample 105. In one embodiment, signal line 109 may be a metal interconnect existing within the dielectric isolation layer of an integrated circuit die. Although tip 103 of cantilever 101 does not necessarily come in direct contact with surface 107 in one embodiment, tip 103 is capacitively coupled to signal line 109.

For purposes of this disclosure, it is appreciated that a signal line encompasses any element carrying an electrical sample waveform to be measured. This includes, but is not limited to actual circuit devices, or portions thereof. Therefore, periodic sample waveforms may also be measured from, for example, the gates of transistors or other integrated circuit elements in accordance with the teachings of the present invention.

Trigger 129 generates a trigger 131, which in one embodiment is used by sample driver 127 when driving the sample waveform in signal line 109. In one embodiment, sample driver 127 and trigger 129 are included in a tester, such as for example automated testing equipment (ATE). In one embodiment, sample driver 127 drives a set of N-bit long test vectors to the pins (not shown) of sample 105 to drive the sample waveform that is carried in signal line 109.

In one embodiment, a composite probe waveform generator 113 generates a composite probe waveform 123. In one embodiment, composite probe waveform 123 is coupled to be received by tip 103 of cantilever 101 through a signal path 111.

Figure 2:
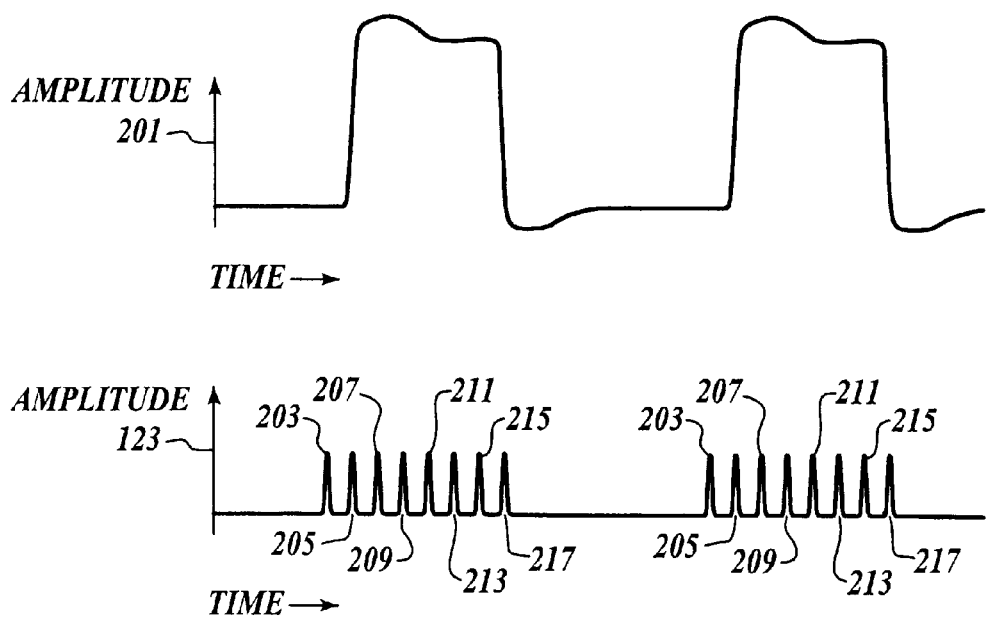
FIG. 2 is a timing diagram showing various waveforms associated with one embodiment of a non-contact waveform measurement apparatus in accordance with the teachings of the present invention.

FIG. 2 is a diagram illustrating the relationship between one example of a composite probe waveform 123 and a sample waveform 201, which is carried by signal line 109 of sample 105. As shown in FIG. 2, composite probe waveform 123 in one embodiment includes a plurality of overlapping component probe waveforms. In the example illustrated in FIG. 2, composite probe waveform 123 includes component probe waveforms 203, 205, 207, 209, 211, 213, 215 and 217. It is appreciated that composite probe waveform 123 may include a greater or fewer number of component probe waveforms in accordance with the teachings of the present invention. As can be noted from FIG. 2, each component probe waveform 203, 205, 207, 209, 211, 213, 215 and 217 have repetition rates or frequencies substantially equal to the repetition rate or frequency of sample waveform 201. In one embodiment, each of the component probe waveforms 203, 205, 207, 209, 211, 213, 215 and 217 of composite probe waveform 123 are modulated at separate modulation frequencies. In one embodiment, the frequencies at which component probe waveforms 203, 205, 207, 209, 211, 213, 215 and 217 are modulated are near a mechanical resonance frequency of cantilever 101.

Referring back to FIG. 1, it is noted that sample generator 127 and composite probe waveform generator 113 are able to generate the sample waveform and component probe waveforms 203, 205, 207, 209, 211, 213, 215 and 217 of composite probe waveform 123 with substantially the same repetition rates because both sample generator 127 and composite probe waveform generator 113 are driven by trigger signal 131 from trigger 129. In another embodiment, trigger 129 is included as part of sample generator 127 and/or composite probe waveform generator 113.

As is known to those skilled in the art, the electrical interaction between tip 103 of cantilever 101 and signal line 109 of sample 105 can be approximated as a capacitor with the voltage difference between 103 and signal line 109 giving rise to an attractive force F 137. It is observed that the force F 137 is proportional to the square of the voltage difference between tip 103 and signal line 109. As a result, the voltage impressed upon tip 103 by composite probe waveform generator 113 generates the corresponding force F 137. In one embodiment, cantilever 101 is configured such that force F 137 results in motion of cantilever 101. In one embodiment, motion detector 135 is configured to detect motion of cantilever 101. In one embodiment, motion detector 135 is optically coupled to cantilever 101 to detect motion of cantilever 101. In one embodiment, motion detector 135 is directly coupled to cantilever 101 to detect motion of cantilever 101.

In one embodiment, the sample waveform may be determined using known techniques by monitoring the gradient or higher order derivatives of force F 137. In another embodiment, the sample waveform may be determined using known techniques by monitoring the vertical or horizontal forces or force gradients of force F 137.

As discussed above, each component probe waveform 203, 205, 207, 209, 211, 213, 215 and 217 is modulated at a frequency substantially less than the repetition rate or frequency of sample waveform 201. In one embodiment, the repetition rates or frequencies at which the component probe waveforms 203, 205, 207, 209, 211, 213, 215 and 217 are modulated are near a mechanical resonance frequency of cantilever 101. In one embodiment, component probe waveforms 203, 205, 207, 209, 211, 213, 215 and 217 are configured to be "on" during one portion of a cycle and "off" during the remaining portion of a cycle. As such, force F 137 is periodically impressed upon cantilever 101 at a repetition rate equal to the repetition rate of the sample waveform 201. During the "off" portion of the modulation cycle of each component probe waveform 203, 205, 207, 209, 211, 213, 215 and 217, the force F 137 impressed upon cantilever 101 is changed.

The differing amounts of force F 137 impressed upon cantilever 101 during the "on" and "off" portions in one embodiment result in motion of cantilever 101 at a frequency near the modulation frequencies of component probe waveforms 203, 205, 207, 209, 211, 213, 215 and 217. In one embodiment, the motion or deflection of cantilever 101 is dependent on mechanical properties of cantilever 101 and the magnitude and driving repetition rate of the driving force F 137. In one embodiment, motion detector 135 is coupled to cantilever 101 to monitor the motion of cantilever 101 using known techniques. By measuring the motion of cantilever 101, the sample waveform in signal line 109 may be determined at the particular points in time within each cycle of the sample waveform that correspond to the points in time when the pulses of each component probe waveform 203, 205, 207, 209, 211, 213, 215 and 217 of component probe waveform 123 are impressed upon tip 103. It is appreciated that because each of the overlapping component probe waveforms 203, 205, 207, 209, 211, 213, 215 and 217 are concurrently impressed upon tip 103 of cantilever 101, the acquisition of sample data points is faster than if only a single composite probe waveform was impressed upon the tip 103 of cantilever 101 at a time.

Although in the above-described embodiment, component probe waveforms 203, 205, 207, 209, 211, 213, 215 and 217 are modulated at frequencies near a mechanical resonance frequency of cantilever 101, it is noted that the component probe waveforms 203, 205, 207, 209, 211, 213, 215 and 217 may be modulated at other frequencies such as for example frequencies higher than the mechanical resonance frequencies of cantilever 101, such as for example but not limited to the harmonics of the fundamental mechanical resonant frequencies of cantilever 101. In other embodiments, it is noted that the modulation frequency of component probe waveforms 203, 205, 207, 209, 211, 213, 215 and 217 may also be less than the fundamental mechanical resonance frequency of cantilever 101 down to DC values. In addition, it is noted that although components probe waveforms 203, 205, 207, 209, 211, 213, 215 and 217 are illustrated in FIG. 2 as nonoverlapping or time separate waveforms, in other embodiments, the component probe waveforms may overlap. In such embodiments, the hardware the present invention would be configured to be able to accommodate the higher voltages or amplitudes resulting from the overlapping individual component probe waveforms.

Figure 3:
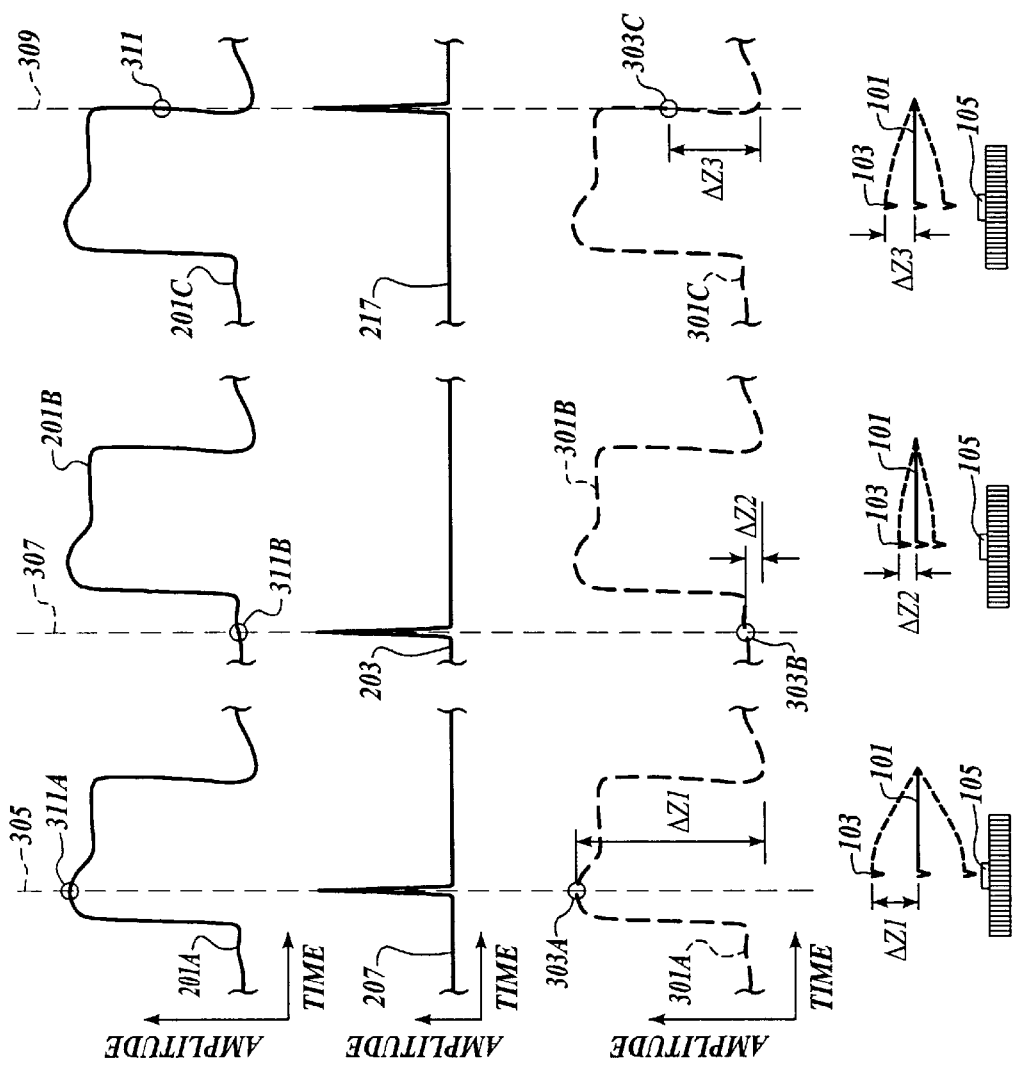
FIG. 3 is a timing diagram showing various waveforms associated with one embodiment of the present invention that further illustrate the principle of operation of one embodiment of a non-contact waveform measurement apparatus in accordance with the teachings of the present invention.

FIG. 3 is a diagram to illustrate the relationship between the motion of cantilever 101 in connection with the component probe waveforms of composite probe waveform 123 and sample waveform 201 in accordance with the teachings of the present invention. In particular, dashed line 305 of FIG. 3 shows that cantilever 101 is displaced an amplitude ΔZ1 relative to sample 105 with the pulse of component probe waveform 207 occurring at the time corresponding to location 311A in sample waveform 201A. Accordingly, a reconstructed waveform value 303A is determined for reconstructed waveform 301A.

Similarly, dashed line 307 shows that cantilever 101 is displaced an amplitude ΔZ2 relative to sample 105 with the pulse of component probe waveform 203 being impressed upon the tip of cantilever 101 at the time corresponding to location 311B in sample waveform 201B. Accordingly, reconstructed waveform value 303B is determined for reconstructed waveform 301B.

Dashed line 309 of FIG. 3 also shows that cantilever 101 is displaced an amplitude of ΔZ3 relative to sample 105 when the pulse of component probe waveform 217 arrives at the tip 103 of cantilever 101 at the time corresponding to location 311C in sample waveform 201C. Accordingly, reconstructed waveform value 303C is determined for reconstructed waveform 301C.

Thus, after determining reconstructed values 303A, 303B, 303C, etc., the sample waveform 201 in sample 105 may be determined in accordance with the teachings of the present invention without having to come in direct contact with sample 105.

Figure 4:
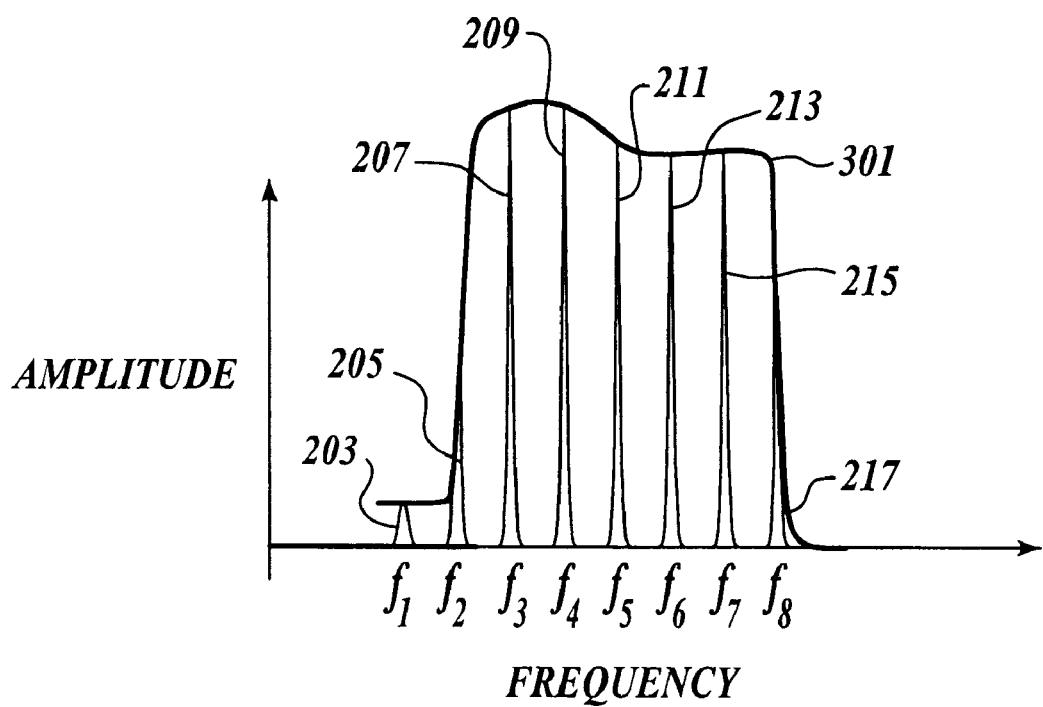
FIG. 4 is a diagram showing a reconstructed sample waveform utilizing one embodiment of a non-contact waveform measurement apparatus in accordance with the teachings of the present invention.

FIG. 4 is an illustration showing a reconstructed waveform 301 based upon component probe waveforms 203, 205, 207, 209, 211, 213, 215 and 217 of composite probe waveform 123. As illustrated in FIG. 4, component probe waveforms 203, 205, 207, 209, 211, 213, 215 and 217 are modulated at frequencies $f_1$, $f_2$, $f_3$, $f_4$, $f_5$, $f_6$, $f_7$ and $f_8$, respectively. In one embodiment, motion detector 135 detects motion of cantilever 101 and demodulates the detected motion at frequencies $f_1$, $f_2$, ..., etc. to determine the motion resulting from each component probe waveform of composite probe waveform 123, which results in reconstructed waveform 301 of FIG. 4.

Figure 5:
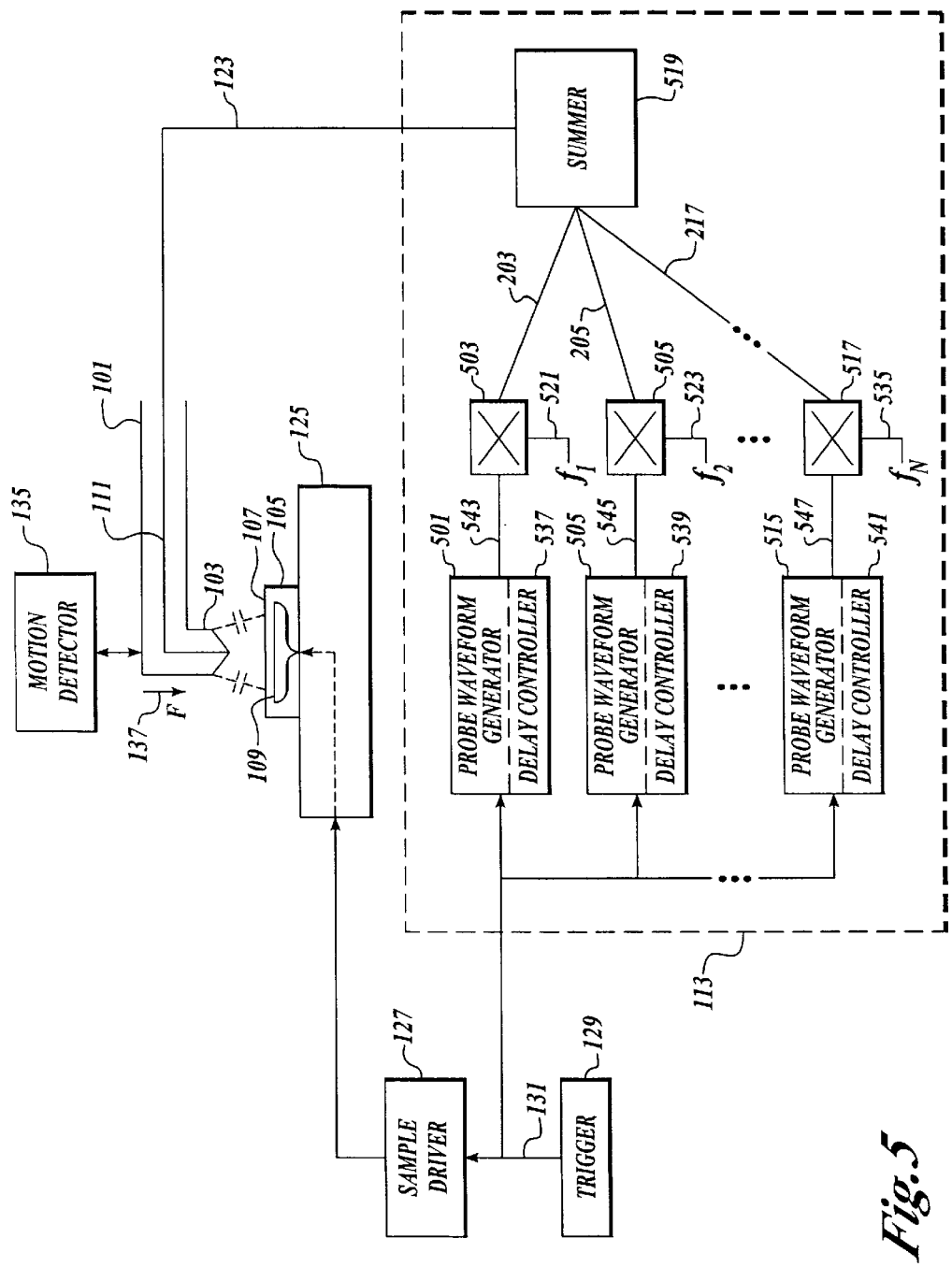
FIG. 5 is a block diagram of another embodiment of a non-contact waveform measurement apparatus in accordance with the teachings of the present invention.

FIG. 5 is a block diagram of another embodiment of a non-contact waveform measurement apparatus in accordance with the teachings of the present invention. The non-contact waveform measurement apparatus of FIG. 5 is similar to the non-contact waveform measurement apparatus illustrated in FIG. 1. FIG. 5 illustrates additional detail for composite probe waveform generator 113. In particular, the embodiment of composite probe waveform generator 113 illustrates a plurality of probe waveform generators 501, 505 and 515 coupled to receive trigger signal 131 from trigger 129. Each probe waveform generator 501, 505 and 515 generate unmodulated component probe waveforms 543, 545 and 547, respectively. Modulator 503 modulates unmodulated component probe waveform 543 in response to modulation frequency $f_1$ 521 and produces component probe waveform 203. Modulator 505 modulates unmodulated component probe waveform 545 in response to modulation frequency $f_2$ 523 and generates component probe waveform 205. Modulator 517 modulates unmodulated component probe waveform 547 in response to modulation frequency $f_N$ 535 and generates component probe waveform 217. In one embodiment, modulator 503, 505 and 517 are implemented using AND gates, switches, multipliers, or the like. Component probe waveforms 203, 205 and 217 are coupled to be received by summer 519, which generates composite probe waveform 123 as a result.

Figure 6:
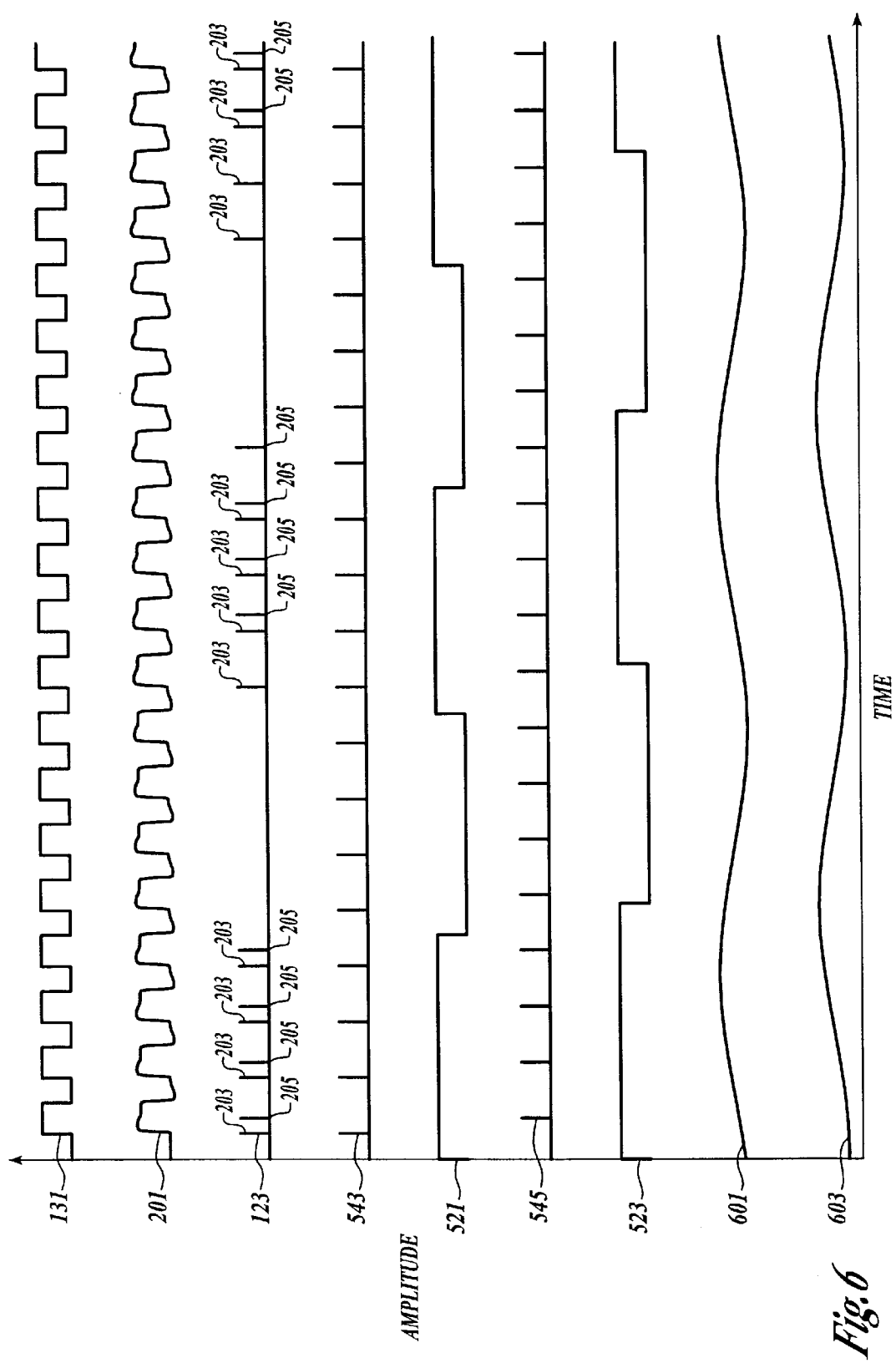
FIG. 6 is a timing diagram showing various waveforms associated with one embodiment of a non-contact waveform measurement apparatus in accordance with the teachings of the present invention.

FIG. 6 is a timing diagram illustrating the relationship of the various waveforms associated with one embodiment of a non-contact waveform measurement apparatus in accordance with the teachings of the present invention. In particular, FIG. 6 shows one embodiment of a trigger signal 131 in relation to a sample waveform 201, which in one embodiment is the sample waveform carried in signal line 109 of FIGS. 1 and 5. As shown in FIG. 6, trigger signal 131, sample waveform 201, unmodulated component probe waveform 543 and unmodulated component probe waveform 545 all have substantially the same repetition rates. As discussed earlier, component probe waveform 203 is generated as a result of unmodulated component probe waveform 543 being modulated in response to frequency $f_1$ 521. Component probe waveform 205 is generated as a result of unmodulated component probe waveform 545 being modulated in response to modulation frequency $f_2$ 523. As shown in FIG. 6, composite probe waveform 123 is generated in one embodiment as the sum of each of the component probe waveforms 203 and 205. In the diagram illustrated in FIG. 6, composite probe waveform 123 includes two overlapping component waveforms, namely component probe waveform 203 and component probe waveform 205. It is appreciated that composite probe waveform 123 may include greater or fewer numbers of component probe waveforms in accordance with the teachings of the present invention.

As shown in the embodiment illustrated in FIG. 6, the pulses of the electrical pulse train of unmodulated component probe waveform 543 are impressed upon tip 103 during an "on" portion of a cycle of modulation frequency 521. The pulses of the electrical pulse train of unmodulated component probe waveform 545 are impressed upon tip 103 during an "on" portion of a cycle of modulation frequency 523. In one embodiment, "on" and "off" condition of modulation frequencies 521 and 523 are "high" and "low" conditions, respectively. It is appreciated that in another embodiment, "on" and "off" conditions of modulation frequencies 521 and 523 may be "low" and "high" conditions, respectively.

Since the pulses of each component probe waveform 203 and 205 have the same repetition rate as sample waveform 201, each component pulse of composite probe waveform 123 is impressed upon tip 103 of cantilever 101 at the same point in time within each cycle of sample waveform 201 during the "on" portion of each respective modulation signal 521 and 523, respectively. Cantilever 101 is therefore displaced varying amounts as a result of the varying forces F 137 over time. Waveform 601 of FIG. 6 shows the displacement of cantilever 101 as a result of component probe waveform 203. Waveform 603 shows the displacement of cantilever 101 over time as a result of component probe waveform 205. In one embodiment, the amount that cantilever 101 is displaced is proportional to the voltage of sample waveform 201 at the time at which the electrical pulses of component probe waveforms 203 and 205 of composite probe waveform 123 are impressed upon tip 103 of cantilever 101.

Referring back to FIG. 5, it is noted that in another embodiment, each probe waveform generator 501, 505 and 515 include a delay controller 537, 539 and 541, respectively. Each delay controller 537, 539 and 541 may be used to adjust the delay of each respective unmodulated component probe waveform 543, 545 and 547, respectively. As a result, the time reference of probe waveform 115 may be adjusted relative to the sample waveform 201 on signal line 109. By adjusting the time reference, the time at which the pulses of each respective component probe waveform 203, 205 and 217 arrive at tip 103 may be adjusted or shifted in time within each cycle of the sample waveform 201 accordingly. As a result, the presently described non-contact waveform measurement apparatus is able to determine values of the sample waveform on signal line 109 at various instances within the cycle of the sample waveform in accordance with the teachings of the present invention.

In addition, it is also noted that by concurrently or simultaneously stimulating tip 103 of cantilever 101 with the overlapping component probe waveforms 203, 205 and 217, and by modulating each of the component probe waveforms at different frequencies, the rate of data acquisition of sampling signal 201 is increased in comparison with other waveform sampling techniques that stimulate the tip 103 of cantilever 101 with only one probe waveform at a time.

Figure 7:
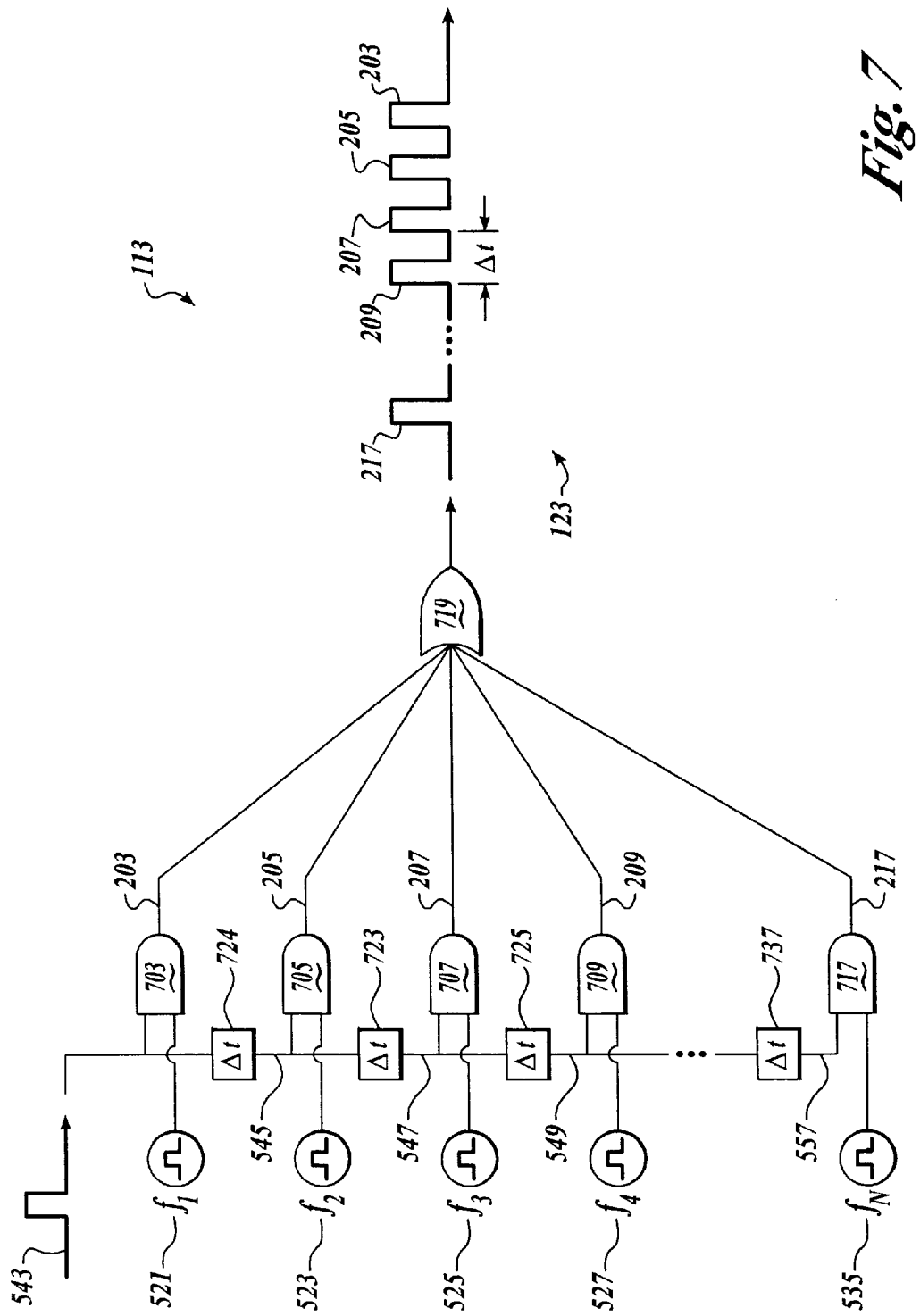
FIG. 7 is a block diagram of yet another embodiment of a non-contact waveform measurement apparatus in accordance with the teachings of the present invention.

FIG. 7 is a block diagram of yet another embodiment of a non-contact waveform measurement apparatus in accordance with the teachings of the present invention. As shown in FIG. 7, a plurality of delays 721, 723, 725 and 737 are cascaded and coupled to receive unmodulated component probe waveforms signal 543. As shown in FIG. 7, each delay 721, 723, 725 and 737 introduces a Δt delay in the received signal. Therefore, unmodulated component probe waveform signal 543 is delayed by Δt to produce component probe waveform signal 545 at the output of delay 721. Similarly, unmodulated component probe waveform signals 547, 549 and 557 are generated at the outputs of delays 723, 725 and 737, respectively. In one embodiment, it is noted that the pulse of unmodulated component probe waveform signal 557 is generated before the next pulse of unmodulated component probe waveform 543 is received at the input of delay 721. Stated differently, in one embodiment, the sum of all of the delays Δt of delays 721, 723, 725 and 737 is less than the period of sample waveform 201.

As shown in FIG. 7, modulators 703, 705, 707, 709 and 717 are coupled to receive unmodulated component probe waveform signals 543, 545, 547, 549 and 557, respectively. In addition, modulators 703, 705, 707, 709 and 717 are also coupled to receive modulation signals $f_1$521, $f_2$523, $f_3$525, $f_4$527 and $f_N$535, respectively. In one embodiment, modulator 703, 705, 707, 709 and 717 are implemented using AND gates as shown in FIG. 7. Component probe waveform signals 203, 205, 207, 209 and 217 are generated by modulators 703, 705, 707, 709 and 717, respectively. The outputs of each modulator 703, 705, 707, 709 and 717 are in one embodiment each coupled to be received by OR gate 719, as shown in FIG. 7. As a result, OR gate 719 generates composite probe waveform signal 123. As shown in FIG. 7, composite probe waveform 123 includes each of the modulated overlapping component probe waveforms 203, 205, 207, 209 and 217. In the embodiment illustrated, each component probe waveform signal, 203, 205, 207, 209 and 217 is separated in time with a delay of Δt. By using the composite probe waveform signal 123 of FIG. 7, data acquisition of sample waveform 201 may be realized in accordance with the teachings of the present invention.

Figure 8:
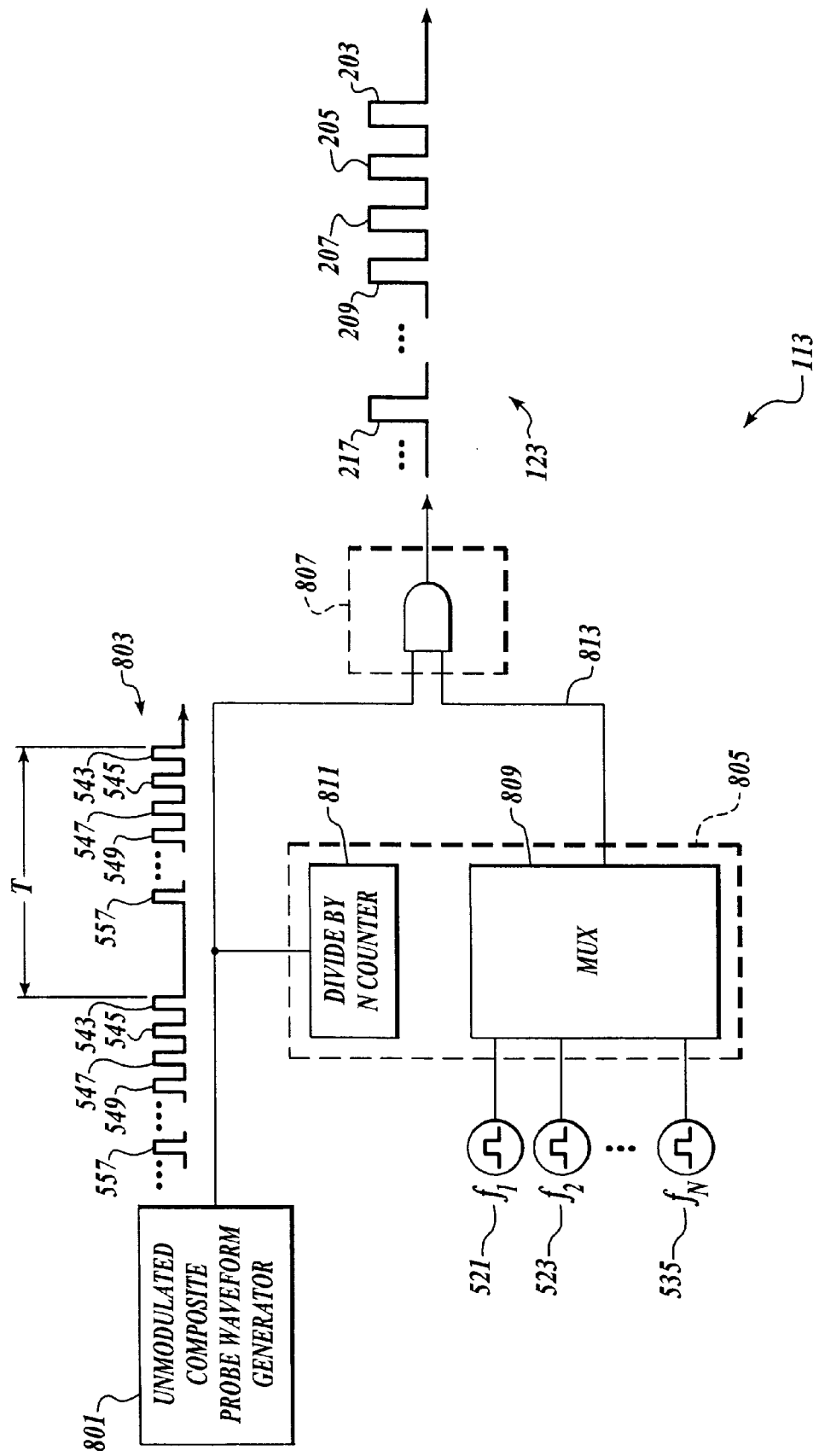
FIG. 8 is a block diagram of yet another embodiment of a non-contact timing waveform measurement apparatus in accordance with the teachings of the present invention.

FIG. 8 is a block diagram of another embodiment of a composite probe waveform generator 113 in accordance with the teachings of the present invention. As shown in FIG. 8, one embodiment of composite probe waveform generator 113 includes an unmodulated composite probe waveform generator 801, which generates an unmodulated composite probe waveform 803. In one embodiment, unmodulated composite probe waveform 803 includes N pulses generated per period T of sample waveform 201. The period T of sample waveform 201 is equal to 1/repetition rate of sample waveform 201. As shown in FIG. 8, unmodulated composite probe waveform 803 includes overlapping unmodulated component probe waveforms 543, 545, 547, 549 and 557. It is noted that the N pulses (unmodulated component probe waveforms 543, 545, 537, 549 and 557) of the unmodulated composite probe waveform 803 are illustrated in FIG. 8 as being unevenly distributed throughout the period T of sample waveform 201. In another embodiment, the N pulses may be evenly distributed throughout the period T of sample waveform 201.

Unmodulated composite probe waveform 803 is coupled to be received by modulator 807. In one embodiment, modulator 807 is implemented using an AND gate, but other embodiments of modulator 807 may be implemented using switches, multipliers or the like. Modulator 807 is configured to modulate each individual component probe waveform 543, 545, 547, 549 and 557 of unmodulated composite probe waveform 803 in response to a modulation signal 813, which is generated by selector 805. Selector 805 is coupled to receive unmodulated composite probe waveform 803 and modulation signals $f_1$521, $f_1$523 and $f_N$535. In one embodiment, selector 805 selects the appropriate modulation signal $f_1$521, $f_2$523, ... $f_N$535 to modulate unmodulated composite probe waveform 803 in response to unmodulated composite probe waveform 803.

In particular, when unmodulated component probe waveform 543 is received at modulator 807, selector 805 selects modulation signal $f_1$521 to modulate unmodulated component probe waveform 543. When unmodulated component probe waveform 545 is received by modulator 807, selector 805 selects modulation signal $f_2$523. As a result, composite probe waveform 123 is output by modulator 807, which is then coupled to be received by tip 103 of cantilever 101. As shown in FIG. 8, composite probe waveform 123 includes overlapping component probe waveforms 203, 205, 207, 209 and 217, which are separately modulated by modulation signals $f_1$521, $f_2$523, ... $f_N$535.

In one embodiment, selector 805 includes a divide by N counter 811 coupled to receive unmodulated composite probe waveform 803. The output of divide by N counter 811 is coupled to be received by multiplexer 809 which selects the appropriate modulation signal $f_1$521, $f_2$ 523, ... $F_N$535. Thus, modulation signal 813 is selected in accordance with one embodiment of the teachings of the present invention.

Therefore, a non-contact waveform measurement apparatus for measuring periodic electrical signal waveforms on or near the surface of a sample is realized. In the foregoing detailed description, the method and apparatus of the present invention has been described with reference to specific exemplary embodiments thereof. It will, however, be evident that various modifications and changes may be made thereto without departing from the broader spirit and scope of the present invention. The present specification and figures are accordingly to be regarded as illustrative rather than restrictive.

What is claimed is:

1. An apparatus for measuring a sample waveform in a signal line proximate to a surface of a sample, the sample waveform having a sample repetition rate, the apparatus comprising:

a cantilever disposed near and spaced apart from the surface of the sample such that the cantilever is capacitively coupled to the signal line;

a composite probe waveform generator to generate a composite probe waveform coupled to be received by the cantilever, the composite probe waveform having first and second probe waveform components, the first and second probe waveform components to be modulated at first and second modulation frequencies, respectively, the first and second probe waveform components having first and second probe repetition rates substantially equal to the sample repetition rate, the first and second modulation frequencies substantially less than the sample repetition rate; and a motion detector coupled to the cantilever, the motion detector to detect a motion of the cantilever.

2. The apparatus of claim 1 wherein the composite probe waveform generator includes first and second probe waveform generators coupled to generate the first and second probe waveform components.

3. The apparatus of claim 2 wherein the composite probe waveform generator further includes first and second probe waveform modulators coupled to the first and second probe waveform generators, respectively, the first probe waveform modulator to modulate the first probe waveform component at the first modulation frequency, the second probe waveform modulator to modulate the second probe waveform component at the second modulation frequency.

4. The apparatus of claim 3 wherein the composite probe waveform generator further includes a summer coupled to the cantilever and the first and second probe waveform modulators, the summer to sum the modulated first probe waveform component and the modulated second probe waveform component to provide the composite probe waveform to the cantilever.

5. The apparatus of claim 1 further comprising:
a sample driver coupled to the sample, the sample driver to drive the sample waveform in the signal line of the sample; and
a trigger to generate a trigger signal having the sample repetition rate, the trigger coupled to the sample driver and the component probe waveform generator, the sample driver to drive the sample waveform in response to the trigger signal and the component probe waveform generator to generate the first and second probe waveform components, respectively, in response to the trigger signal.

6. The apparatus of claim 1 wherein the component probe waveform generator includes first and second delay controllers, the first delay controller to adjust a first time delay difference between the first probe waveform component and the sample waveform, the second delay controller to adjust a second time delay difference between the second probe waveform component and the sample waveform.

7. The apparatus of claim 5 wherein the sample driver includes a delay controller, the delay controller to adjust a time delay difference between the first and second probe waveform components and the sample waveform.

8. The apparatus of claim 1 wherein the first and second modulation frequencies are approximately equal to a mechanical resonance frequency of the cantilever.

9. The apparatus of claim 1 wherein the first and second modulation frequencies are approximately equal to a harmonic of a mechanical resonance frequency of the cantilever.

10. The apparatus of claim 3 wherein the first and second modulators comprise first and second gates, respectively.

11. The apparatus of claim 3 wherein the first and second modulators comprise first and second switches, respectively.

12. The apparatus of claim 3 wherein the first and second modulators comprise first and second multipliers, respectively.

13. The apparatus of claim 4 wherein the summer comprises a logical-OR gate.

14. The apparatus of claim 2 wherein the second probe waveform generator includes a delay circuit coupled to the first probe waveform generator to generate the second probe waveform component.

15. The apparatus of claim 1 wherein the composite probe waveform generator comprises:
a probe waveform generator to generate an unmodulated composite probe waveform N pulses of per period of the sample waveform;
a selector coupled to select among N modulation signals in response to the unmodulated composite probe waveform, the selector to generate an unmodulated composite probe waveform modulation signal; and
a modulator to generate the composite probe waveform in response to the unmodulated composite probe waveform and the unmodulated composite probe waveform modulation signal.

16. The apparatus of claim 15 wherein the selector comprises:
a divide by N counter coupled to receive the unmodulated composite probe waveform; and
a multiplexer coupled to select among the N modulation signals in response to the divide by N counter, the multiplexer to generate the unmodulated composite probe waveform modulation signal.

17. The apparatus of claim 15 wherein the modulator comprises an AND gate.

18. A method of measuring a sample waveform in a signal line proximate to a surface of a sample, the sample waveform having a sample repetition rate, the method comprising:
providing a cantilever to be disposed near and spaced apart from the surface of the sample such that the cantilever is capacitively coupled to the signal line;
coupling the cantilever to receive a composite probe waveform having first and second probe waveform components, the first and second probe waveform components to be modulated at first and second modulation frequencies, respectively, the first and second probe waveform components having first and second probe repetition rates substantially equal to the sample repetition rate, the first and second modulation frequencies substantially less than the sample repetition rate; and
configuring motion of the cantilever to be measured resulting from a voltage difference in the capacitive coupling between the cantilever and the signal line of the sample.

19. The method of claim 18 wherein coupling the cantilever to receive the composite probe waveform having the first and second probe waveform components comprises generating the first and second probe waveform components.

20. The method of claim 19 wherein coupling the cantilever to receive the composite probe waveform having the first and second probe waveform components comprises modulating the first and second probe waveform components.

21. The method of claim 20 wherein coupling the cantilever to receive the composite probe waveform having the first and second probe waveform components comprises summing the modulated first and second probe waveform components.

22. The method of claim 18 further comprising:
generating a trigger signal having the sample repetition rate;
driving the sample waveform in response to the trigger signal; and generating the first and second probe waveform components of the component probe waveform in response to the trigger signal.

23. The method of claim 18 further comprising adjusting a time delay difference between the first and second probe waveform components and the sample waveform.

24. The method of claim 18 wherein coupling the cantilever to receive the composite probe waveform having the first and second probe waveform components comprises:

generating an unmodulated composite probe waveform having the first and second probe waveform components; and modulating the first and second probe waveform components of the unmodulated composite probe waveform at the first and second modulation frequencies, respectively.

* * * * *